United States Patent
Cherkassky et al.

(10) Patent No.: US 10,120,005 B2
(45) Date of Patent: *Nov. 6, 2018

(54) SYNCHRONOUS DETECTION CIRCUIT AND METHOD FOR DETERMINING A BIO-IMPEDANCE OF A BIOLOGICAL TISSUE

(71) Applicant: Silicon Laboratories Inc., Austin, TX (US)

(72) Inventors: Alexander Cherkassky, Hollis, NH (US); Bruce P. Del Signore, Hollis, NH (US)

(73) Assignee: Silicon Laboratories Inc., Austin, TX (US)

(*) Notice: Subject to any disclaimer, the term of this patent is extended or adjusted under 35 U.S.C. 154(b) by 245 days.

This patent is subject to a terminal disclaimer.

(21) Appl. No.: 15/258,461

(22) Filed: Sep. 7, 2016

(65) Prior Publication Data
US 2018/0067063 A1  Mar. 8, 2018

(51) Int. Cl.
*G01R 27/00* (2006.01)
*A61B 5/053* (2006.01)
(Continued)

(52) U.S. Cl.
CPC ............ *G01R 27/00* (2013.01); *A61B 5/053* (2013.01); *A61B 5/7225* (2013.01);
(Continued)

(58) Field of Classification Search
CPC ........ G01R 27/00; G01R 27/02; G01N 27/04; A61B 5/0537; A61B 5/053
(Continued)

(56) References Cited

U.S. PATENT DOCUMENTS 5,963,160 A   10/1999 Wilson et al.
6,795,007 B2   9/2004 Mayes
(Continued)

OTHER PUBLICATIONS

Wikipedia, "Delta-sigma modulation", printed from internet on Nov. 1, 2016, 15pp.
(Continued)

*Primary Examiner* — Amy He
(74) *Attorney, Agent, or Firm* — Egan Peterman Enders Huston

(57) ABSTRACT

Embodiments of synchronous detection circuits and methods are provided for extracting magnitude and phase information from a waveform. One embodiment of a synchronous detection circuit includes a driver circuit, an analog-to-digital converter (ADC) and a controller. The driver circuit is configured to supply an input waveform at an input frequency to a load. The ADC is coupled to receive an output waveform from the load, and configured for generating four digital samples, each spaced 90° apart, for every period of the output waveform. The controller is configured for setting an oversampling rate (OSR) of the ADC, so that the ADC generates an integer number, M, of sub-samples for each digital sample generated by the ADC, where the integer number, M, of sub-samples is inversely proportional to the input frequency of the input waveform. The controller is further configured to use the digital samples generated by the ADC to extract magnitude and phase information from the output waveform.

22 Claims, 4 Drawing Sheets

(51) Int. Cl.
| | |
|---|---|
| G01N 27/04 | (2006.01) |
| G01R 19/00 | (2006.01) |
| A61B 5/00 | (2006.01) |
| G01R 25/00 | (2006.01) |
| G01R 27/02 | (2006.01) |
| A61B 5/024 | (2006.01) |
| A61B 5/08 | (2006.01) |

(52) U.S. Cl.
CPC ........... *A61B 5/7278* (2013.01); *G01N 27/04* (2013.01); *G01R 19/0038* (2013.01); *G01R 25/005* (2013.01); *G01R 27/02* (2013.01); *A61B 5/0002* (2013.01); *A61B 5/024* (2013.01); *A61B 5/0537* (2013.01); *A61B 5/0816* (2013.01)

(58) Field of Classification Search
USPC ........................................ 324/600, 609, 622
See application file for complete search history.

(56) References Cited

U.S. PATENT DOCUMENTS

| | | | |
|---|---|---|---|
| 7,880,655 B2 | 2/2011 | Danner et al. | |
| 2003/0006782 A1* | 1/2003 | Shambroom | A61B 5/0476 324/614 |
| 2005/0283091 A1* | 12/2005 | Kink | A61B 5/0537 600/547 |
| 2012/0098520 A1* | 4/2012 | Rossi | A61B 5/04002 324/76.77 |
| 2018/0067154 A1 | 3/2018 | Cherkassky et al. | |

OTHER PUBLICATIONS

Wikipedia, "Instrumentation amplifier", printed from internet on Nov. 1, 2016, 3pp.
Baker, "How delta-sigma ADCs work, Part 1", Analog Applications Journal, 3Q 2011, 6pp.
Baker, "How delta-sigma ADCs work, Part 2", Analog Application Journal, 4Q 2011, 5pp.
Bertemes-Filho et al., "Low power current sources for bioimpedance measurements: a comparison between Howland and OTA-based CMOS circuits", Journal of Electrical Bioimpedance, Oct. 23, 2012, 8pp.
Cao et al., "A Bioimpedance Measurement System with Low-Power Compressive Sampling Time-Based A/D Converter", posted on the ECE Georgia Tech website: http://mgh-courses.ece.gatech.edu/ece6414/S13/Projects/Team4_Draft1_ECE6414_S13.pdf downloaded on Nov. 1, 2016, 4pp.
Kamat et al., :A Heart Rate Measurement using Bioimpedance Signal Analysis, International Journal of Advanced Research in Electrical, Electronics and Instrumentation Engineering, Apr. 2014, 6pp.
Pandey et al., "New Tetrapolar Method for Complex Bioimpedance Measurement", International Journal of Current Engineering and Technology, Jun. 2014, 3pp.
Rossi et al., "A low power Bioimpedance module for wearable systems", Science Direct, 2014, 4pp.
Yang et al., "Design and preliminary evaluation of a portable device for the measurement of Bioimpedance spectroscopy", Institute of Physics Publishing, Oct. 25, 2006, 17pp.
Yang et al., "New Tetrapolar Method for Complex Bioimpedance Measurement: Theoretical Analysis and Circuit Realization", Conference Proceedings: Annual International Conference of the IEEE Engineering in Medicine and Biology Society, Jan. 2005, 4pp.
Analog Devices, "Data Sheet AD5933, 1 MSPS, 12-Bit Impedance Converter, Network Analyzer", Last content update Aug. 30, 2016, 40pp.
Randall, Terence Cordell, "A Low-Power, Reconfigurable, Pipelined ADC with Automatic Adaptation for Implantable Bioimpedance Applications", PhD Diss, University of Tennessee, 2014, 169pp.
Allen, "Lecture 390—Oversampling ADCS—Part I", CMOS Analog Circuit Design, 2010, 14pp.
Aziz et al., "An Overview of Sigma-Delta Converters: How a 1-bit ADC achieves more than 16-bit resolution", Jan. 1996, 26pp.
A. Kipnis, A. Goldsmith, and Y. Eldar, "Optimal trade-off between sampling rate and quantization precision in sigma-delta a/d conversion," in Sampling Theory and Applications (SampTA), 2015 International Conference on, May 2015, pp. 627-631.
Cho et al., "A Boi-Impedance Measurement System for Portable Monitoring of Heart Rate and Pulse Wave Velocity Using Small Body Area", IEEE Pub 978-1-4244-3828-0/09, 2009, 4pp.
Luna-Lozano et al., "Portable Device for Heart Rate Monitoring Based on Impedance Pletysmography", IEEE Pub 978-1-4799-6230-3/14, 2014, 4pp.
Seoane at al., "An analog front-end enables electrical impedance spectroscopy system on-chip for biomedical applications", Physiological Measurement, Jul. 2008, 13pp.
Steve Bush, "Novel synchronous detector digs signals out of noise", Electronics Weekly.com, Oct. 30, 2014, 8pp.

\* cited by examiner

| F_IN | M | N | OSR | valid OSR |
|---|---|---|---|---|
| 100kHz | 52 | 1 | 52 | --- |
| 90kHz | 58 | 1 | 58 | --- |
| 80kHz | 66 | 1 | 66 | --- |
| 70kHz | 75 | 1 | 75 | --- |
| 60kHz | 88 | 1 | 88 | --- |
| 50kHz | 105 | 1 | 105 | --- |
| 40kHz | 66 | 2 | 132 | --- |
| 30kHz | 88 | 2 | 176 | --- |
| 20kHz | 66 | 4 | 264 | --- |
| 10kHz | 66 | 8 | 528 | 264 |
| 9kHz | 73 | 8 | 584 | 292 |
| 8kHz | 82 | 8 | 656 | 328 |
| 7kHz | 94 | 8 | 752 | 376 |
| 6kHz | 109 | 8 | 872 | 436 |
| 5kHz | 66 | 16 | 1056 | 264 |
| 4kHz | 82 | 16 | 1312 | 328 |
| 3kHz | 109 | 16 | 1744 | 436 |
| 2kHz | 82 | 32 | 2624 | 328 |
| 1kHz | 82 | 64 | 5248 | 328 |

SYNCHRONOUS DETECTION CIRCUIT AND METHOD FOR DETERMINING A BIO-IMPEDANCE OF A BIOLOGICAL TISSUE

BACKGROUND

1. Field of the Disclosure

This disclosure relates to synchronous detection circuits and, more particularly, to a low-power, high accuracy synchronous detection circuit and method for determining a bio-impedance of a biological tissue.

2. Description of the Relevant Art

The following descriptions and examples are provided as background only and are intended to reveal information that is believed to be of possible relevance to the present disclosure. No admission is necessarily intended, or should be construed, that any of the following information constitutes prior art impacting the patentable character of the subject matter claimed herein.

Electrical bio-impedance measurements have been widely used as a non-invasive technique for characterizing biological tissues, detecting heart rate, determining body composition, and ascertaining other physiological states and conditions. Bio-impedance is the opposition offered by biological tissues to the current flowing through them, and is typically measured by injecting an alternating current of known amplitude and frequency into a biological tissue and detecting a voltage waveform therefrom. The injected current signal (also referred to as an excitation signal or carrier signal) is modulated in amplitude and phase by the impedance of the biological tissue under test. A complex bio-impedance signal having an in-phase component (I) and a quadrature component (Q) is determined from the voltage waveform. The in-phase component is the resistive component or real part of the bio-impedance signal, and the quadrature component is the reactive component or imaginary part of the bio-impedance signal.

Synchronous detection circuits are often used for extracting small signals, such as bio-impedance signals, which may be buried in the noise floor of a measurement signal. Synchronous detection can be implemented in a variety of different ways. A block diagram of a conventional synchronous detection circuit 10 commonly used for detecting bio-impedance signals is shown in FIG. 1.

In the synchronous detection circuit shown in FIG. 1, a voltage controlled current source (VCCS) 12 is used to inject an alternating current ($I_0$) at a carrier frequency ($\omega_0$) into a biological tissue through an outer pair of electrodes 14. The voltage differential ($V_Z$) detected across an inner pair of electrodes 16 is detected and amplified by an instrumentation amplifier (IA) 18. While detected at the same carrier frequency ($\omega_0$) as the injected current ($I_0$), the voltage waveform ($V_m$) generated by the instrumentation amplifier 18 is modulated in both magnitude ($|V_m|$) and phase ($\theta$) by the impedance of the biological tissue.

To extract the real and imaginary components of the complex bio-impedance signal, the voltage waveform ($V_m$) is supplied to pair of mixers 20, where it is multiplied (demodulated) with in-phase (I) and quadrature (Q) reference signals. The I and Q signals are synchronized to the carrier frequency ($\omega_0$), but phase shifted by 0° and 90° respectively. The demodulated signals ($V_1$ and $V_2$) are supplied to low-pass filters (LPF) 22 for rejecting noise over the carrier frequency, and digitized by analog-to-digital converters (ADC) 24 to produce the real ($Z_{real}$) and imaginary ($Z_{imag}$) components of the bio-impedance signal. These components are then used to calculate the magnitude and relative phase of the bio-impedance signal according to equations (1) and (2) below, from which useful health information may be derived.

$$\text{Magnitude} = \sqrt{Z_{real}^2 + Z_{imag}^2} \qquad \text{EQ. 1}$$

$$\text{Phase} = \tan^{-1}(1/Z_{real}) \qquad \text{EQ. 2}$$

There are numerous problems associated with the synchronous detection circuit shown in FIG. 1. First, the carrier frequencies used in bio-impedance measurements typically range from about 1 kHz to 100 kHz, or more. In order to detect bio-impedance over such a wide range of frequencies, the bandwidth of the current driver 12 and the instrumentation amplifier 18 must be large, which leads to large power consumption. In order to reject noise over different bio-impedance frequencies, the bandwidth of the low pass filters 22 included within the I and Q channels would need to be changed for each carrier frequency. This is difficult when analog filters are used, and is generally not done over a large number of frequencies, due to the increase in circuit complexity and size required for each additional frequency. Furthermore, the circuit shown in FIG. 1 relies on analog mixers in the I and Q channels to convert the voltage waveform ($V_m$) into DC signals ($V_1$ and $V_2$). Any mismatch between the analog circuits within the two channels will cause large phase errors and reduce the accuracy of the bio-impedance measurement. In addition, conventional techniques utilize two analog to digital converters operating simultaneously (one per I or Q channel) which is a drawback, due to the expense of an additional analog to digital converter and any additional resulting channel mismatch.

An efficient, low-power synchronous detection circuit and method for conducting bio-impedance measurements would be well-suited to wearable biometric monitoring devices, such as smart watches, fitness bands, health trackers, and other smart wearable devices. Existing bio-impedance instruments used in clinical environments are bulky, expensive, user-unfriendly, power hungry, and cannot be used in continuous consumer health monitoring applications. The electronic components typically used in clinical bio-impedance instruments are limited in injection current frequency, have large power consumption and/or require additional components, which make such components unsuitable for low-power and/or continuous consumer health monitoring applications. Although wearable bio-impedance alternatives exist, these devices often lack accuracy and repeatability, thereby precluding their use even in low-end consumer applications.

SUMMARY

The following description of various embodiments of synchronous detection circuits and methods is not to be construed in any way as limiting the subject matter of the appended claims.

Generally speaking, the present disclosure provides a highly efficient, low power, low cost synchronous detection circuit, which demonstrates greater accuracy and measurement reliability than currently available circuits. Embodiments of synchronous detection circuits and methods described herein may be broadly used for extracting magnitude and phase information from substantially any amplitude and/or phase modulated waveform. According to one particular embodiment, the disclosed circuits and methods may be used for determining a bio-impedance of a biological tissue by extracting magnitude and phase information from a voltage waveform.

In general, the embodiments of synchronous detection circuits disclosed herein may include a driver circuit, an analog-to-digital converter (ADC) and a controller. The driver circuit may be generally coupled for supplying an alternating current signal at an input frequency to a first pair of electrodes in contact with a biological tissue. The ADC may be coupled for receiving a voltage waveform from a second pair of electrodes in contact with the biological tissue, and may be configured for generating digital samples therefrom. According to one embodiment, the ADC may be configured for generating four digital samples of the output waveform per period of the output waveform, such that one digital sample is generated within each of the four quadrants. The techniques described herein are particularly advantages for use with a sigma-delta ADC as such ADCs break the conversions into many sub-samples which may be utilized as described in more detail herein.

The controller may be coupled for controlling the operation of the ADC. According to one embodiment, the controller may be configured for setting an oversampling rate (OSR) of the ADC equal to a decimating rate (DR) of the ADC, so that the ADC generates an integer number, M, of sub-samples during each quadrant of the voltage waveform, which are used to generate one digital sample per quadrant of the output waveform. The integer number, M, of sub-samples may be inversely proportional to the input frequency of the input waveform.

According to one embodiment, the controller may be configured for determining the bio-impedance of the biological tissue by using the digital samples generated by the ADC to determine a magnitude and phase of the voltage waveform. In some embodiments, the controller may use the four digital samples generated per period of the voltage waveform to calculate new magnitude and phase values every period of the voltage waveform. In other embodiments, the controller may average the four digital samples generated over a number, P, of periods of the voltage waveform, and may use the averaged digital samples to calculate new magnitude and phase values every P periods of the voltage waveform.

As described in more detail below, high efficiency and low power consumption are achieved in the embodiments of synchronous detection circuits described herein by extracting magnitude and phase information from only four digital samples per period of the output waveform. High accuracy and measurement reliability are achieved by resolving both the input waveform and the output waveform into M coarse points and N interpolation points per quadrant, and matching the OSR and the DR of the ADC to the input frequency of the input waveform. By setting the OSR and the DR of the ADC to some integer multiple of M (e.g., N*M), where M is inversely proportional to the frequency of the input waveform, the ADC may be configured to output continuous time averaged samples at 1 sample per quadrant without artifacts. At some input frequencies, the OSR of the ADC may be reduced to a valid OSR (e.g., N*M/X, where X is an integer value greater than or equal to 2) to provide continuous time averaged sampling at 2 or more samples per quadrant and avoid exceeding the limitations of the ADC.

BRIEF DESCRIPTION OF THE DRAWINGS

Other objects and advantages of the disclosure will become apparent upon reading the following detailed description and upon reference to the accompanying drawings.

Figure 1:
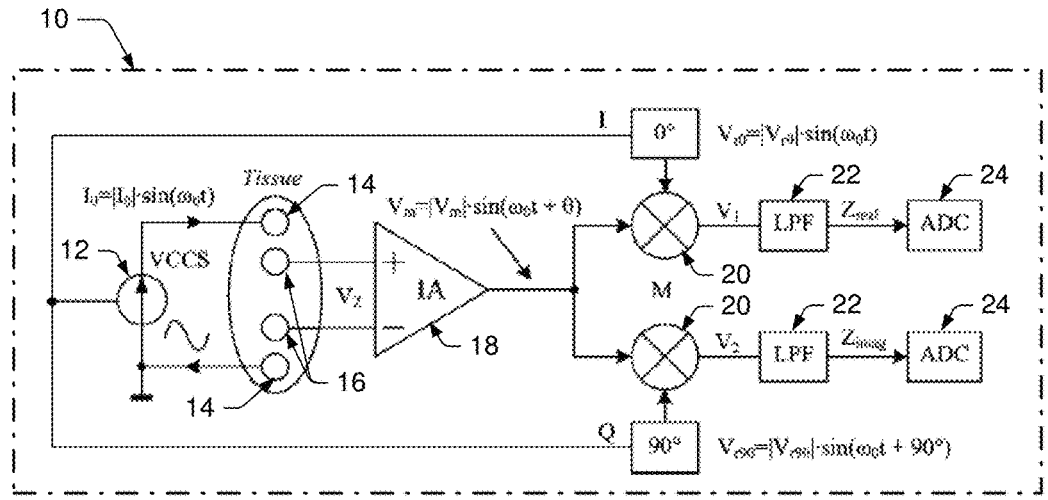
FIG. 1 is a block diagram illustrating one embodiment of a conventional synchronous detection circuit.

While the synchronous detection circuits and methods disclosed herein are susceptible to various modifications and alternative forms, specific embodiments thereof are shown by way of example in the drawings and will herein be described in detail. It should be understood, however, that the drawings and detailed description thereto are not intended to limit the disclosure to the particular form disclosed, but on the contrary, the intention is to cover all modifications, equivalents and alternatives falling within the spirit and scope of the present disclosure as defined by the appended claims.

DETAILED DESCRIPTION OF PREFERRED EMBODIMENTS

In general, the present disclosure is directed to synchronous detection circuits and methods for extracting magnitude and phase information from a waveform. Embodiments of the disclosed circuits and methods may be broadly used for extracting such information from substantially any amplitude and/or phase modulated signal. According to one embodiment, the disclosed circuits and methods may be used for extracting magnitude and phase information from a bio-impedance waveform. Regardless of application or use, the embodiments of synchronous detection circuits and methods disclosed herein provide a low power, low cost synchronous detection circuit, which demonstrates greater accuracy and measurement reliability than many currently available solutions.

According to one embodiment, the present disclosure may be directed to biometric monitoring devices, which are typically (although not exclusively) designed to be worn by a user continuously, intermittently or during certain activities (e.g., while exercising). On the other hand, the present disclosure may be directed to non-wearable biometric monitoring devices. These devices may be incorporated into various consumer health devices (e.g., bathroom scales), fitness equipment and clinical instrumentation. As such, these devices are typically larger and not designed to be used on a continual or regular basis.

Wearable biometric monitoring devices are usually smaller in size, so as to be relatively unobtrusive for the wearer, and are typically designed to be worn for long periods of time without discomfort. These devices may be worn on a variety of different body parts including, for example, a user's wrist, arm, ankle, leg or chest, without interfering with the user's range of motion or daily activities.

As such, a wearable biometric monitoring device may be provided in a variety of form factors including various configurations of bands or straps, which are sized to accommodate a user's wrist, arm, ankle, leg or chest, and configured to compress the device against the user's skin. Alternatively, a wearable biometric monitoring device may be attached to a user's clothing, or may be inserted into a wearable sleeve, sock or compression band that compresses the device against the user's skin.

Regardless of size or use, biometric monitoring device may collect and/or derive data corresponding to the wearer's physiological state, physical state and/or surrounding environment. As such, a biometric monitoring device may include a variety of biometric and environmental sensors for collecting and/or deriving data pertaining to heart rate, blood pressure, oxygen saturation, respiration rate, skin and/or body temperature, calories burned, floors ascended/descended, ambulatory speed and/or distance traveled, light exposure, geographic location, heading and/or elevation, etc. In addition to one or more biometric and environmental sensors, a biometric monitoring device may also include circuitry for sampling, digitizing and/or filtering the sensor signals, a processor or other control circuitry for controlling sensor functionality, processing the data collected by the sensors and/or deriving information pertaining the wearer's physiological state, physical state and/or environment, and a memory for storing program instructions executable by the processor for implementing such functionality and/or for temporarily or persistently storing the collected/processed/derived data. In some cases, a biometric monitoring device may also include a user interface for displaying the collected/processed/derived data and/or for displaying user configuration options. Additionally or alternatively, a biometric monitoring device may include a communication interface (e.g., wired or wireless) for communicating with a client or external device.

Figure 2:
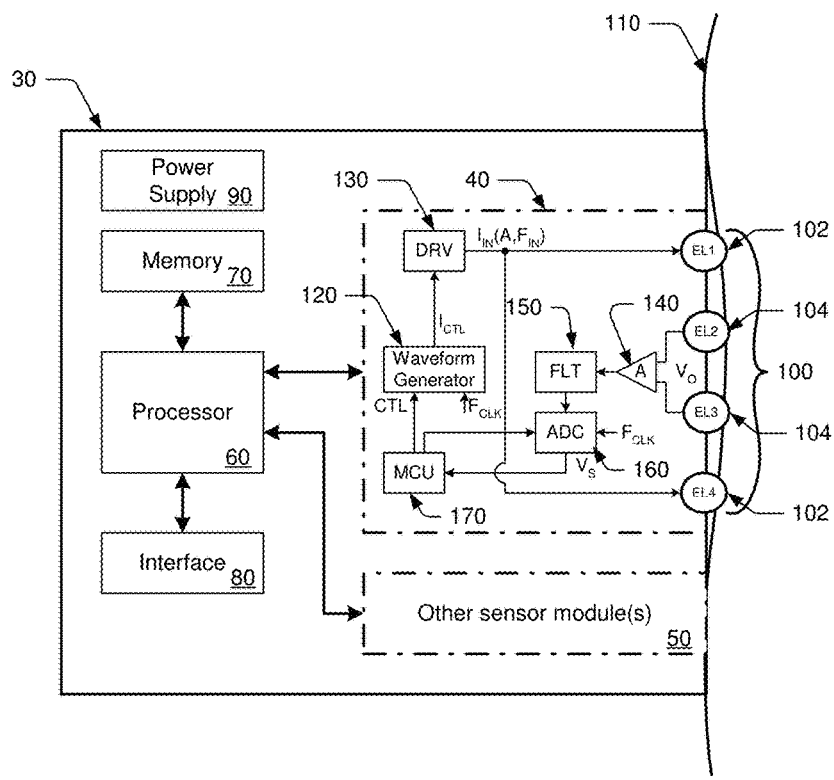
FIG. 2 is a block diagram illustrating one embodiment of a biometric monitoring device comprising an improved synchronous detection circuit, according to one embodiment.

FIG. 2 is a block diagram illustrating various components of a biometric monitoring device 30, according to one exemplary embodiment. Biometric monitoring device 30 may be a wearable device, a non-wearable device or an implantable device. Although certain components of the biometric monitoring device are illustrated and described herein for purposes of demonstrating various features and functionality of the disclosed device, one skilled in the art would understand and appreciate that additional and/or alternative components may be included without departing from the scope of the disclosed embodiments.

As shown in FIG. 2, biometric monitoring device 30 generally includes one or more sensor modules 40, 50, a processor 60, a memory 70, an interface 80 and a power supply 90. The one or more sensor modules 40, 50 are generally configured for collecting data pertaining to a wearer's physiological state, physical state and/or surrounding environment. Processor 60 is generally configured for controlling the functionality of the biometric monitoring device 30, processing the data collected by the sensor modules and/or deriving information pertaining to the wearer's physiological state, physical state and/or environment based on the collected data. Memory 70 is generally configured for storing program instructions, which are executable by the processor 60 for implementing such functionality, and/or for temporarily or persistently storing the collected, processed and/or derived data. In some embodiments, interface 80 may be a user interface, which is configured for displaying the collected, processed and/or derived data, and/or for displaying user configuration options. In other embodiments, interface 80 may additionally or alternatively comprise a communication interface (e.g., wired or wireless communication interface) for communicating the collected, processed and/or derived data to an external device or application. Power supply 90 may comprise a battery for supplying power to the components of the biometric monitoring device 30, and in some cases, may comprise additional circuitry for regulating or rectifying the current or voltage provided by the battery to one or more components of the biometric monitoring device 30. In some embodiments, power supply 90 may comprise additional circuitry for charging a rechargeable battery.

In the particular embodiment shown in FIG. 2, biometric monitoring device 30 includes synchronous detection circuit 40, and optionally, one or more additional sensor modules 50. Synchronous detection circuit 40 is generally configured for extracting amplitude and phase information from a waveform. When incorporated within a biometric monitoring device 30, the synchronous detection circuit 40 (otherwise referred to as bio-impedance sensor module) may be used for detecting bio-impedance signals from a user's skin or other biological tissue 110, and extracting amplitude and phase information from the detected bio-impedance signals, so that useful health information can be derived. Examples of health information that may be derived from the extracted amplitude and phase information include, but are not limited to, heart rate (HR) and respiration rate data. Others health information may include are body fat and dehydration. Moreover, bio-impedance may be utilized for analysis of numerous other health and biological factors, and the techniques described herein are described merely as exemplary uses of bio-impedance data.

Examples of additional sensor modules 50 that may be included within the biometric monitoring device 30 include, but are not limited to, a photoplethysmographic (PPG) sensor, a temperature sensor, an electrocardiographic sensor (ECG or EKG), a skin galvanic response sensor (DC resistance of skin), a motion detection sensor (e.g., an accelerometer, gyroscopic sensor, or global positioning system, GPS), an ambient light sensor, etc. Although additional sensor modules 50 may be included within the biometric monitoring device of FIG. 2, these modules may be omitted in other embodiments.

As shown in FIG. 2, synchronous detection circuit 40 may include a plurality of electrodes 100, which are mounted on or embedded within an external surface of the biometric monitoring device 30, so that the electrodes 100 are in contact with the biological tissue 110 when the device is in use. The particular embodiment shown in FIG. 2 is based on a tetrapolar (four electrode) structure, in which two electrodes (e.g., the outer electrodes) 102 are used for injecting an alternating current into the biological tissue 110, and two electrodes (e.g., the inner electrodes) 104 are used in the detection of a bio-impedance signal. As shown in FIG. 2, a waveform generator 120 and driver 130 are included within synchronous detection circuit 40 for generating and supplying a sinusoidal varying injection current signal of amplitude, A, and frequency, $F_{IN}$, to the outer electrodes 102.

In some embodiments, a single injection current of fixed amplitude, frequency and/or phase may be supplied to the outer electrodes 102 by the waveform generator 120 and driver 130. The amplitude and/or frequency of the injection current signal may depend on several factors including, but not limited to, the desired health information to be derived from the bio-impedance signal, the desired signal-to-noise ratio (SNR) of the detected bio-impedance signal, associated safety limitations placed on the injection current, the quality of the skin-electrode contact, and the power supply headroom available to driver 130.

In some embodiments, an injection current of variable amplitude, frequency and/or phase may be supplied to the outer electrodes 102 by waveform generator 120 and driver 130. In one example, the amplitude of the injection current signal may be adjusted to improve the SNR of the detected bio-impedance signal by maximizing the headroom available to driver 130. As described in more detail below, the available headroom may be subject to safety limitations and contact impedance fluctuations caused by loss or poor contact between the electrodes 100 and the biological tissue 110. Injecting electrode contact impedance increases greatly as frequency is decreased. Thus, more current may be "pumped" at higher frequencies thus increasing the SNR greatly. In another example, the frequency of the injection current signal may be adjusted as phase information may be more sensitive at certain frequency ranges. In yet another example, the frequency of the injection current signal may be swept across an injection frequency range (e.g., about 1 kHz to about 100 kHz, or some subset thereof) to enable spectral analysis of the bio-impedance signal (otherwise referred to as bio-impedance spectroscopy) to be conducted. Spectral analysis may be conducted on-chip or off-chip and may be used to monitor the pathological status of biological tissues, such as performed in bio-impedance spectroscopy (BIS). BIS may be used to measure intra-cell fluid (ICF), extra-cell fluid (ECF), total body water (TBW) and other biological factors.

As the injection current signal passes through one or more biological tissues (e.g., skin, adipose tissue, blood vessels, heart muscle, etc.), the amplitude and phase of the injection signal is modulated by the impedance of those tissue(s). This bio-impedance signal is detected across inner electrodes 104 as a sinusoidal varying output voltage waveform ($V_O$), which is amplified by amplifier 140, filtered by filter 150 and digitized by analog-to-digital converter (ADC) 160.

In the embodiment shown in FIG. 2, ADC 160 is coupled for providing a number of digital samples ($V_S$) to an on-chip controller (e.g., a microcontroller unit, or MCU) 170. In some embodiments, the on-chip controller 170 may use the digital samples to extract magnitude and phase information from the detected bio-impedance (voltage) waveform ($V_O$). Alternatively, ADC 160 may supply the digital samples to an off-chip controller or microprocessor (such as processor 60, for example) for extracting the magnitude and phase information. In either case, controller 170 is preferably coupled and configured to provide additional functionality to synchronous detection circuit 40. Such functionality may include, but is not limited to, controlling the injection current provided by waveform generator 120 and driver 130, and selecting/controlling characteristics of ADC 160 to provide an efficient, low-power sampling scheme.

Synchronous detection circuit 40 improves upon the conventional synchronous detection circuit 10 shown in FIG. 1, in one respect, by utilizing a direct sampled, synchronous detection topology that eliminates the need for well-matched analog components (such as mixers 20 and LFPs 22) and dual ADCs 24, which are required in I/Q extraction techniques. This not only reduces circuit complexity, size and cost, but also reduces and/or eliminates the phase errors that are often introduced by such analog components.

As described in more detail below, synchronous detection circuit 40 provides a mostly digital topology, which enables the injection current to be programmed over a wide range of injection current frequencies and amplitudes. Unlike synchronous detection circuit 10, which provides limited injection frequencies due to the use of analog filters 22 in the I/Q channels, the programmable injection frequencies provided by synchronous detection circuit 40 enable bio-impedance spectroscopy to be easily performed by on- or off-chip components.

In addition, synchronous detection circuit 40 provides a more efficient, lower-power circuit and method for sampling the bio-impedance waveform and extracting the relevant magnitude/phase information therefrom than conventional circuits and methods. In addition to improved efficiency and power consumption, synchronous detection circuit 40 also enables magnitude and phase information to be extracted from the bio-impedance waveform with substantially higher accuracy and measurement reliability, and shorter time duration, than conventional circuits and methods. Further details of the improved synchronous detection circuit and extraction method described herein, and the advantages afforded thereby, are discussed below in reference to FIGS. 3-6.

Figure 3:
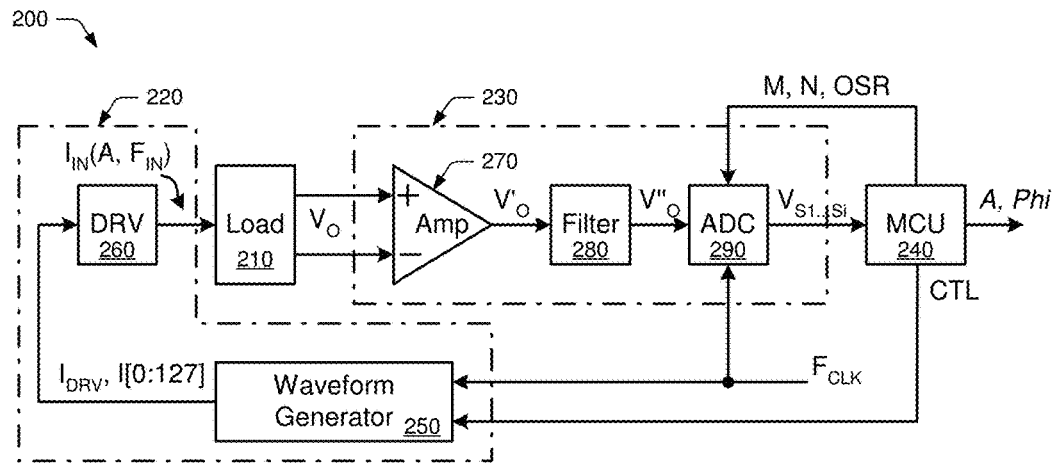
FIG. 3 is a block diagram illustrating one embodiment of an improved synchronous detection circuit.

FIG. 3 is a block diagram illustrating an improved synchronous detection circuit 200, according to one embodiment. In some cases, synchronous detection circuit 200 may be incorporated within a biometric monitoring device (such as, e.g., biometric monitoring device 30 of FIG. 2) for detecting and/or monitoring bio-impedance signals from a biological tissue. When synchronous detection circuit 200 is used for detecting bio-impedance signals, an injection current signal may be supplied to a load 210 through one pair of electrodes (e.g., outer electrodes 102 of FIG. 2), and a bio-impedance signal may be detected from the load 210 through another pair of electrodes (e.g., inner electrodes 104 of FIG. 2). The load 210 may be a user's skin or other biological tissue(s), such as adipose tissue, blood vessels, heart muscle, etc., depending on how/where the biometric monitoring device is used.

It is noted, however, that synchronous detection circuit 200 is not strictly limited to the detection of bio-impedance signals, and may be alternatively used for extracting magnitude and phase information from other output waveforms ($V_O$) detected from a load 210. When used for detecting other output waveforms, load 210 may be substantially any medium that modulates an alternating signal or carries an amplitude/phase modulated signal. Example loads may include, but are not limited to, electronic instrumentation for which measurements of a complex response of an unknown network are desired. When synchronous detection circuit 200 is used for detecting a complex resistive, inductive and/or capacitive load, for example, a signal may be supplied to the load 210 (e.g., and unknown electronic network), and a complex response signal may be detected from the load 210.

As shown in FIG. 3, synchronous detection circuit 200 generally includes a transmit stage 220, a receive stage 230 and a controller 240 for controlling the operation of the transmit and receive stages. Transmit stage 220 is generally configured to generate and supply an input waveform having amplitude, A, and frequency, $F_{IN}$, to the load 210. Receive stage 230 is generally configured to receive an output waveform having a modulated amplitude and/or phase from the load 210, and to produce a number of digital samples from the modulated output waveform. Although the transmit and receive stages may be configured for supplying and receiving many different types of input and output waveforms, the transmit and receive stages will be described herein as respectively configured for supplying a sinusoidal varying injection current signal ($I_{IN}$) to the load 210, and receiving a modulated voltage waveform ($V_O$) from the load 210 from which digital samples ($V_S$) are produced. One skilled in the art will understand how the nomenclature may change when the transmit and receive stages are configured for supplying and receiving different types of input and output waveforms.

In the embodiment shown in FIG. 3, transmit stage 220 includes waveform generator 250 and driver 260, and receive stage 230 includes amplifier 270, filter 280 and analog-to-digital converter (ADC) 290. The waveform generator 250 in the transmit stage 220 and the ADC 290 in the receive stage 230 are preferably synchronized to the same clock signal frequency ($F_{CLK}$). Although substantially any clock frequency may be used, the clock frequency supplied to waveform generator 250 and ADC 290 may be approximately 21 MHz, in one example.

As shown in FIG. 3, transmit stage 220 receives a control signal (CTL) from controller 240 for generating a sinusoidal varying injection current signal ($I_{IN}$) having a programmable amplitude, A, frequency, $F_{IN}$, and phase. According to one embodiment, waveform generator 250 may be a digital signal processor (DSP)-based waveform generator and driver 260 may be a current-controlled, digital-to-analog converter (I-DAC) having a number of programmable current levels. Although respectively described herein as a DSP-based waveform generator and I-DAC, waveform generator 250 and driver 260 are not strictly limited to such, and may be alternatively implemented in other embodiments. For example, one method may be to generate a square wave and filter it to produce sinusoid results (the filter preferably being frequency specific). Other methods may use "function generator" techniques, such as diodes that do piece-wise linear approximation to a sinusoid.

In general, waveform generator 250 may be configured to generate a sinusoidal waveform ($I_{DRV}$) at a programmable input frequency, $F_{IN}$, and phase, which is specified by the control signal (CTL) received from the controller 240. The sinusoidal waveform ($I_{DRV}$) generated by waveform generator 250 may be supplied to driver 260, along with a digital signal (I[0:x]), which may be used for controlling the amplitude (A) of the sinusoidal varying injection current signal ($I_{IN}$) produced by the driver. According to one embodiment, driver 260 may be a 7-bit I-DAC having 128 programmable current levels, which may be selected by a 7-bit digital signal (e.g., I[0:127]).

Although not strictly limited to such, the programmable input frequency, $F_{IN}$, may be selected from a range of available frequencies from about 1 kHz to about 100 kHz. In some embodiments, the range of available frequencies may comprise a number of discrete frequencies from about 1 kHz to about 10 kHz in 1 kHz increments, and a number of discrete frequencies from about 10 kHz to about 100 kHz in 10 kHz increments. It is noted, however, that the range of available frequencies is not strictly limited to any particular number of discrete frequencies or any particular frequency range, and may differ depending on application or use of synchronous detection circuit 200.

For each input frequency ($F_{IN}$) within the range of available frequencies, waveform generator 250 may be configured to divide each period (T) of the sinusoidal waveform ($I_{DRV}$) into four equal quadrants, and resolve each quadrant into a number (M) of coarse points and a number (N) of interpolation points. In doing so, waveform generator 250 may use M*N pulses of the clock frequency, $F_{CLK}$, to generate each quadrant of the sinusoidal waveform ($I_{DRV}$). As described in more detail below, this waveform information ($F_{IN}$, M, and N) may be stored in memory for each input frequency ($F_{IN}$) within the range of available frequencies, and may be used in the receive stage 230 for controlling the operation of the ADC 290.

The current amplitude selected for use by the digital signal (I[0:x]) may depend on several factors, such as the desired health information to be derived from the bio-impedance signal, the desired signal-to-noise ratio (SNR) of the detected bio-impedance signal, associated safety limitations placed on the injection current, the quality of the skin-electrode contact, and the power supply headroom available to the driver 260. In some embodiments, a desired current amplitude may be determined from a voltage differential measurement detected, for example, across the two outer electrodes 102 shown in FIG. 2. In one example embodiment, waveform generator 250 may initially be configured provide a digital signal (I[0:x]) corresponding to a relatively small drive current amplitude (A) to driver 260, and may monitor the voltage differential detected across the outer electrodes 102. Thereafter, the waveform generator 250 may gradually or incrementally increase the value of the digital signal supplied to the driver 260 to increase the current amplitude generated thereby until the voltage differential detected across the outer electrodes 102 meets or exceeds a threshold value. In one example, the threshold value may correspond to a maximum allowable drive current level, which is constrained by safety limitations and power supply headroom.

As shown in FIG. 3, the amplifier 270 within receive stage 230 receives the modulated voltage waveform ($V_O$) from the load 210 and produces an amplified voltage waveform ($V_O'$), which is supplied to filter 280. According to one embodiment, amplifier 270 may be an instrumentation amplifier (IA) having programmable gain and reference voltages, and filter 280 may be an anti-aliasing filter, which is configured to limit the bandwidth of the filtered waveform ($V_O''$) supplied to the ADC 290. Although described herein as comprising an instrumentation amplifier and anti-aliasing filter, it is noted that receive stage 230 is not strictly limited to such, and may be alternatively implemented in other embodiments.

ADC 290 is coupled to receive the filtered waveform ($V_O''$) output from filter 280 and configured to produce a number of digital samples ($V_{S1}, \ldots V_{S1}$) therefrom. According to one embodiment, ADC 290 may be configured to generate four digital samples ($V_{S1}, V_{S2}, V_{S3}, V_{S4}$), each spaced 90° apart, for every period (T) of the filtered output waveform ($V_O''$). This functionality is depicted in the exemplary waveform illustrated in FIG. 4. Like the input waveform ($I_{IN}$), each period (T) of the filtered output waveform ($V_O''$) may be divided into four equal quadrants ($Q_1, Q_2, Q_3, Q_4$). As described in more detail below, ADC 290 is preferably configured to generate four digital samples ($V_{S1}, V_{S2}, V_{S3}, V_{S4}$) from the filtered output waveform ($V_O''$), so that one digital sample is generated within each of the four quadrants ($Q_1, Q_2, Q_3, Q_4$).

In some embodiments, the digital samples ($V_{S1}, V_{S2}, V_{S3}, V_{S4}$) obtained from the filtered output waveform ($V_O''$) may be supplied directly to controller 240 for extracting magnitude and phase information according to equations (3) and (4) below.

$$\text{Magnitude} = \frac{1}{2}\sqrt{(V_{S1} - V_{S3})^2 + (V_{S2} - V_{S4})^2} \qquad \text{EQ. 3}$$

-continued $$\text{Phase} = \tan^{-1}\left(\frac{V_{S2} - V_{S4}}{V_{S1} - V_{S3}}\right) \quad \text{EQ. 4}$$

In such embodiments, controller 240 may use the four digital samples ($V_{S1}$, $V_{S2}$, $V_{S3}$, $V_{S4}$) to generate new magnitude and phase values for every period (T) of the filtered output waveform (V0″). This functionality corresponds to performing a fast Fourier transform (FFT) that is obtained for a single frequency of the input frequency ($F_{IN}$) which is one-quarter (¼) of the sampling frequency ($F_S$).

In other embodiments, controller 240 may average the digital samples ($V_{S1}$, $V_{S2}$, $V_{S3}$, $V_{S4}$) over a number (P) of periods of the filtered output waveform (V0″) prior to extracting magnitude and phase information according to equations (5) and (6) below.

$$\text{Magnitude} = \quad \text{EQ. 5}$$

$$\frac{1}{2P}\sqrt{\left(\sum_{p=1}^{P} V_{S1}(p) - \sum_{p=1}^{P} V_{S3}(p)\right)^2 + \left(\sum_{p=1}^{P} V_{S2}(p) - \sum_{p=1}^{P} V_{S4}(p)\right)^2}$$

$$\text{Phase} = \tan^{-1}\left(\frac{\sum_{p=1}^{P} V_{S2}(p) - \sum_{p=1}^{P} V_{S4}(p)}{\sum_{p=1}^{P} V_{S1}(p) - \sum_{p=1}^{P} V_{S3}(p)}\right) \quad \text{EQ. 6}$$

This corresponds to effectively performing P shorter FFT's, instead of one long FFT, on the filtered output waveform (V0″), where each FFT is performed at a sample frequency, $F_S$, of $4*P*F_{IN}$. By averaging the digital samples over a number (P) of periods, the effective noise bandwidth may be reduced by a factor of P. The noise bandwidth reduction applies not just to ADC quantization noise, but to all other sources of input-referred noise (e.g., circuit noise, noise of the input signal, etc.). Because synchronous detection creates excitation at a narrow frequency and detects only that frequency, any noise residing outside this narrow frequency is rejected.

According to one embodiment, ADC 290 may generate four digital samples ($V_{S1}$, $V_{S2}$, $V_{S3}$, $V_{S4}$) during each period (T) of the filtered output waveform (V0″) by oversampling and decimating the filtered output waveform (V0″). For example, ADC 290 may be a sigma-delta (ΣΔ) ADC comprising a ΣΔ modulator, a low pass digital filter function and a decimation filter function. The ΣΔ modulator may be configured to convert the filtered output waveform (V0″) into a 1-bit data stream at an oversampling rate (OSR), which is based on the ADC clock frequency ($F_{CLK}$) and the frequency ($F_{IN}$) of the input waveform ($I_{IN}$) supplied to the load 210. The low-pass digital filter function may be configured to sample the 1-bit data stream to produce a number of sub-samples at a relatively high data rate. The decimation filter function decimates the sub-samples at a decimation rate (DR) to output a number of digital samples ($V_{S1}$, $V_{S2}$, $V_{S3}$, $V_{S4}$) at a reduced data rate of four samples per period (T).

According to one embodiment, controller 240 may be coupled for controlling the operation of ADC 290, such that the oversampling rate (OSR) and the decimation rate (DR) of the ADC are set equal to one another, and matched to the clock frequency ($F_{CLK}$) and the input frequency ($F_{IN}$) of the input waveform ($I_{IN}$) supplied to the load 210. As noted above, ADC 290 and waveform generator 250 are synchronized to the same clock signal frequency ($F_{CLK}$). This clock signal frequency is fixed and may be approximately 21 MHz, in one example. However, the frequency ($F_{IN}$) of the input waveform ($I_{IN}$) supplied to the load 210 is programmable, and may be adjusted throughout a range of input frequencies, as described above. Therefore, it may be necessary to determine appropriate OSR and DR values for each input frequency within the range of available input frequencies, and to control the operation of the ADC 290 according to the particular input frequency being used.

In some cases, controller 240 may control the operation of ADC 290 by adjusting the oversampling rate (OSR) and the decimation rate (DR) of the ADC according to equation (7) below.

$$OSR = DR = \frac{F_{CLK}}{4F_{IN}} \quad \text{EQ. 7}$$

By adjusting the OSR and DR of ADC 290 to account for the variable input frequency ($F_{IN}$), an appropriate OSR and DR can be used to oversample and decimate the filtered output waveform (V0″). In some cases, adjusting the OSR and DR according to equation (7) may produce artifacts in the ADC output when lower input frequencies (e.g., about 1 kHz to about 40 kHz) are supplied to the load 210.

In order to avoid the above mentioned artifacts, controller 240 may adjust the OSR and the DR of ADC 290, so that the ADC generates an integer number, M, of sub-samples for each quadrant ($Q_1$, $Q_2$, $Q_3$, $Q_4$) of the filtered output waveform (V0″), and one digital sample for every M number of sub-samples. This may be achieved, in one embodiment, by resolving each quadrant of the filtered output waveform into a number (M) of coarse points and a number (N) of interpolation points, as done previously by the waveform generator 250 when generating the sinusoidal waveform ($I_{DRV}$). In the case of the filtered output waveform (V0″), however, the number M corresponds to the number of sub-samples produced by ADC 290 within each quadrant, and the number N corresponds to the number of interpolation points between each of the M sub-samples. By setting the OSR and DR of ADC 290 according to equation (8), $$OSR = DR = M*N \quad \text{EQ. 8}$$

controller 240 ensures that the ADC will produce an integer number (M) of sub-samples during each quadrant of the filtered output waveform, wherein the number (M) of sub-samples produced by the ADC corresponds precisely to the number of clock pulses used by waveform generator 250 to generate one quadrant of the sinusoidal waveform ($I_{DRV}$).

Figures 5, 6:
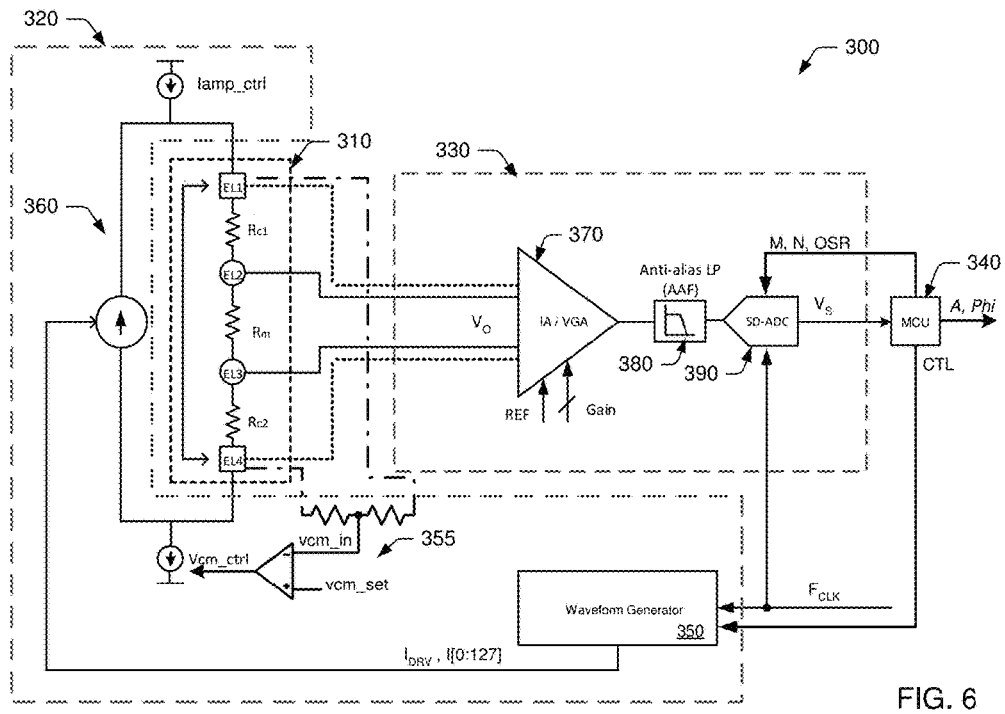
FIG. 5 is an exemplary table of stored values, which may be used by a controller to control characteristics of an ADC.
FIG. 6 is a block diagram illustrating another embodiment of an improved synchronous detection circuit.

Appropriate values for M and N may be predetermined for each input frequency ($F_{IN}$) within a range of input frequencies, and may be stored within a table of values for later use. An exemplary table of stored values relating M, N and OSR to input frequency ($F_{IN}$) is shown in FIG. 5. For each input frequency ($F_{IN}$), M and N may be predetermined by setting equation (7) equal to equation (8) and solving for the nearest value of M as shown in equation (9).

$$M = \frac{F_{CLK}}{4NF_{IN}} \quad \text{EQ. 9}$$

At higher input frequencies (e.g., frequencies between about 50 kHz to about 100 kHz), an interpolation factor of N=1 may be used to determine an appropriate value of M. At lower input frequencies (e.g., frequencies below 50 kHz), the interpolation factor, N, may be increased to ensure that the number of sub-samples, M, does not exceed a maximum value.

According to one embodiment, controller 240 may use the table of stored values for adjusting the OSR and DR of ADC 290 to match or correspond with a particular input frequency ($F_{IN}$) selected for use within the synchronous detection circuit 200. The table of values may generally be stored in memory either residing within, or coupled to, controller 240. In one exemplary embodiment, a table of stored values relating M, N and OSR to input frequency ($F_{IN}$) for the entire range of available input frequencies may be stored within a read-only memory (ROM) component coupled to controller 240. Upon (or subsequent to) configuring the synchronous detection circuit 200 for monitoring a particular input frequency, a subset of the table values corresponding to the particular input frequency may be loaded into, for example, a random access memory (RAM) component residing within controller 240. Alternative means for storing the table values may also be used.

In the exemplary table shown in FIG. 5, appropriate values of M, N and OSR are predetermined and stored within the table for a range of input frequencies ($F_{IN}$) extending from 1 kHz to 100 kHz. The range of input frequencies included within the illustrated table correspond to frequencies commonly used for detecting and monitoring bio-impedance signals. Since the synchronous detection circuit 200 described herein may be used for detecting and monitoring other types of signals, the input frequencies ($F_{IN}$) and associated values of M, N and OSR used for detecting/monitoring such signals may differ from those specifically illustrated in FIG. 5. It should be understood, therefore, that the input frequencies and values depicted in FIG. 5 are provided for illustrative purposes only.

In some embodiments, the table of stored values may ensure that the OSR of ADC 290 and/or the number of sub-samples (M) generated by the ADC per quadrant does/do not exceed a maximum value(s). This may be achieved, in some embodiments, by adjusting the interpolation factor, N, to account for changes in input frequency ($F_{IN}$).

At higher input frequencies (e.g., between about 50 kHz to about 100 kHz), an interpolation factor of N=1 may be specified in the table for producing an OSR and a number, M, of sub-samples that range between 105 (for an input frequency of 50 kHz) and 52 (for an input frequency of 100 kHz). At lower input frequencies (e.g., below 50 kHz), the interpolation factor, N, may be increased to ensure that the number of sub-samples, M, does not exceed roughly 100 sub-samples per quadrant. This is mainly a practical measure to limit the number of entries in the memory table that contains the current DAC values generating the given waveform period. For example, a 1 KHz waveform uses 5000 ADC clocks at 20 MHz to generate 1 quadrant ($250^{-6}*20^6$). Instead of storing 5000 values one can store, for example, 100 values and use 50× interpolation between the adjacent data points. In such cases, certain waveform distortion may be accounted for in SNR calculations. In one example, the interpolation factor, N, may be increased to some integer value greater than 1 for input frequencies below 50 kHz. In another example, the interpolation factor, N, may be increased by a factor of $2^x$, where x is an integer value greater than or equal to 1, for input frequencies below 50 kHz. The value x may be selected to ensure that M does not exceed a maximum value (e.g., roughly 100 sub-samples per quadrant) when M is determined according to equation (9).

At certain low input frequencies (e.g., frequencies of 10 kHz and less), setting the OSR according to equation (8) may exceed a maximum oversampling rate (e.g., 512) of the ADC 290. In these situations, the OSR may be reduced to a "valid" OSR, which may be determined according to equation (10), stored within the table and later used to control the ADC.

$$\text{valid } OSR = \frac{M*N}{X} \qquad \text{EQ. 10}$$

In EQ. 10, 'X' is an integer value equal to or greater than 2. More specifically, integer 'X' is the smallest integer value that results in an integer valid OSR, which is less than or equal to a maximum OSR of the ADC 290. As shown in FIG. 5, for example, an OSR of 528 (M*N=66*8=528) may be specified in the table for an input frequency of 10 kHz. If the ADC has a maximum OSR of 512, for example, an OSR of 528 may cause the ADC to exceed it's maximum OSR. To avoid exceeding the maximum oversampling rate of the ADC at certain input frequencies, the OSR (e.g., 528 at 10 kHz) may be reduced to a valid OSR (e.g., 528/2=264 at 10 kHz), which is supplied to the ADC in lieu of the OSR. By setting the OSR of ADC 290 according to equation (10) at certain lower input frequencies (e.g., frequencies of 10 kHz and less), controller 240 may enable the ADC to generate two or more samples per quadrant, thereby enabling the ADC to output continuous time averaged digital samples without artifacts and without exceeding the limitations of the ADC.

The synchronous detection circuit 200 shown in FIGS. 2-5 and described above provides many advantages and distinctions over conventional synchronous detection circuits and methods for extracting magnitude and phase information from a waveform. As noted above, the synchronous detection circuits described herein improve upon the conventional synchronous detection circuit 10 shown in FIG. 1, in one respect, by utilizing a direct sampled, synchronous detection topology that eliminates the need for the well-matched analog components (such as mixers 20 and LFPs 22) and dual ADCs 24 required in I/Q extraction techniques. This not only reduces circuit complexity, size and cost, but also reduces and/or eliminates the phase errors that are often introduced by such analog components.

In addition, the synchronous detection circuits described herein provide a mostly digital topology, which enables the amplitude, frequency and phase of the input waveform to be programmed over a wide range of amplitudes, frequencies and phase. Although a particular set of frequencies are illustrated in the exemplary table shown in FIG. 5, one skilled in the art would readily understand how a larger/smaller set of frequencies, within the same or a different frequency range, may be used for detecting and monitoring signals from a load.

Furthermore, the synchronous detection circuits described herein provide a more efficient, lower-power circuit and method for sampling an output waveform and extracting the relevant magnitude/phase information than provided by conventional circuits and methods. High efficiency and low power consumption are achieved in the synchronous detection circuits described herein by extracting magnitude and phase information from only four digital samples per period of the output waveform. This reduces power consumption by reducing the processing requirements placed on the controller.

In addition to improved efficiency and power consumption, synchronous detection circuit described herein also enables the magnitude and phase information to be extracted from the output waveform with substantially higher accuracy and measurement reliability, and shorter time duration, than conventional circuits and methods. According to one embodiment, the synchronous detection circuit described herein achieves high accuracy and measurement reliability by resolving both the input waveform and the output waveform into M coarse points and N interpolation points per quadrant, and matching the oversampling rate (OSR) and decimation rate (DR) of the ADC to the input frequency ($F_{IN}$) for continuous time averaged sampling at 1 sample per quadrant, or 4 samples per period of the output waveform. By setting the OSR and the DR of the ADC to some integer multiple of M (e.g., N*M), where M is determined according to equation (9) above, the ADC may be configured to output continuous time averaged samples without artifacts. At some input frequencies, the OSR of the ADC may be reduced to a valid OSR (e.g., N*M/X) to provide continuous time averaged sampling at 2 or more samples per quadrant and avoid exceeding the limitations of the ADC.

In some embodiments, the digital samples output by the ADC may be averaged over a number (P) of periods to reduce the effective noise bandwidth and to recover ADC resolution loss (e.g., caused by reducing OSR to a valid OSR at lower input frequencies). All noise is reduced as effect of this averaging, not just the ADC quantization noise. For example, there may be noise due to the waveform generation, and noise due to the front end, and noise due to the signal being measured. Averaging, or effective digital filtering, is designed to reduce this combined noise, of which the ADC quantization noise is only a portion. However, the more averaging done (or the longer the signal observation time), the more energy that is spent. Thus, reducing observation time will reduce the power consumption, but at the expense of accuracy.

The number (P) of periods depends on the input frequency ($F_{IN}$), and may generally be selected to achieve a desired observation time and noise bandwidth. In one example, the digital samples output by the ADC for a 100 kHz input/output waveform may be averaged over 100 periods to achieve a 1 millisecond observation time and 1 kHz effective noise bandwidth. The same observation time and effective noise bandwidth may be achieved by averaging the digital samples output by the ADC for a 20 kHz input/output waveform over 20 periods. The mostly digital topology of the synchronous detection circuit described herein enables the observation time and noise bandwidth to be adjusted, as desired.

FIG. 6 is a block diagram illustrating one embodiment of a synchronous detection circuit 300, which is specifically designed and used in the detection and monitoring of bio-impedance signals. The synchronous detection circuit 300 shown in FIG. 6 includes many of the same components and features included within the synchronous detection circuit 200 shown in FIGS. 2-5 and described above. As such, synchronous detection circuit 300 provides many of the same advantages and distinctions over conventional synchronous detection circuits and methods as synchronous detection circuit 200. Additional advantages and distinctions are discussed in the description set forth below.

Like the embodiment shown in FIG. 3, the synchronous detection circuit 300 shown in FIG. 6 may generally include a transmit stage 320, a receive stage 330 and a controller 340 for controlling the operation of the transmit and receive stages. Transmit stage 320 is generally configured to generate and supply an input waveform having amplitude, A, and frequency, $F_{IN}$, to the load 310. Receive stage 330 is generally coupled to receive an output waveform having a modulated amplitude and/or phase from the load 310, and is generally configured to produce a number of digital samples from the modulated output waveform.

In the particular embodiment shown in FIG. 6, load 310 comprises a plurality of electrodes (EL1 . . . EL4) in contact with a biological tissue. In order to detect bio-impedance signals from the biological tissue, transmit stage 320 is coupled and configured for supplying a sinusoidal varying injection current signal ($I_{IN}$) to an outer pair of the electrodes (EL1 and EL4), and receive stage 330 is coupled for receiving a modulated voltage waveform ($V_O$) from an inner pair of the electrodes (EL2 and EL3). Receive stage 330 is further configured for producing a number of digital samples ($V_S$) from the modulated voltage waveform.

Like the previously disclosed embodiment, transmit stage 320 includes waveform generator 350 and driver 360, and receive stage 330 includes amplifier 370, filter 380 and analog-to-digital converter (ADC) 390. The waveform generator 350 in the transmit stage 320 and the ADC 390 in the receive stage 330 are synchronized to the same clock signal frequency ($F_{CLK}$), which may be approximately 21 MHz, in one example.

According to one embodiment, waveform generator 350 may be a digital signal processor (DSP)-based waveform generator, which is configured to generate and supply a sinusoidal waveform ($I_{DRV}$) to driver 360. The sinusoidal waveform generated by waveform generator 350 may have a programmable input frequency ($F_{IN}$) and phase, which is specified by a control signal (CTL) supplied to waveform generator 350 by controller 340. The programmable input frequency may be selected from a range of available frequencies (e.g., from about 1 kHz to about 100 kHz), as described above. In addition to the sinusoidal waveform ($I_{DRV}$), waveform generator 350 may be configured to provide a digital signal (e.g., I[0:127]) to driver 360 for controlling the amplitude (A) of the sinusoidal varying injection current signal ($I_{IN}$) produced by driver 360.

According to one embodiment, driver 360 may be a 7-bit current-controlled, digital-to-analog converter (I-DAC) having 128 programmable current levels and low signal distortion (greater than 70 dB SQNR, in one example). A simplified depiction of driver 360 is illustrated in FIG. 6 as an I-DAC comprising three current sources, each composed of 128 digitally selectable current elements with programmable current values. The amplitude (A) of the sinusoidal varying injection current signal ($I_{IN}$) is controlled by supplying the digital signal, I[0:127], to the top current source. As noted above, the current amplitude may depend on several factors, such as the desired health information to be derived from the bio-impedance signal, the desired signal-to-noise ratio (SNR) of the detected bio-impedance signal, associated safety limitations placed on the injection current, the quality of the skin-electrode contact, and the power supply headroom available to driver 360.

In some embodiments, the quality of the skin-electrode contact may be monitored by detecting a voltage differential produced across the outer electrodes (EL1 and EL4), as shown by the dotted lines in FIG. 6. As the contact quality deteriorates, the voltage amplitude across the outer electrodes fluctuates and may rise to exceed an allowed voltage headroom (typically limited by battery and/or supply voltage) of the driver. This voltage amplitude may be continuously, periodically or intermittently determined by using receive stage 330 to sample the voltage waveform obtained from the outer electrodes, and using controller 340 to extract the amplitude of the voltage waveform according to equation (3) or (5), as described above. By monitoring the skin-electrode contact quality in such a manner, the amplitude (A) of the injection current signal ($I_{IN}$) can be adjusted to maintain an optimal injection current level for each state of contact measurement. Alternatively, information can be fed back to the user to request that the skin-electrode contact be adjusted.

In some embodiments, a common-mode voltage (CMV) feedback circuit 355 may be coupled to the bottom current source within driver 360 for sensing a CMV between the outer electrodes (EL1 and EL4) and controlling the CMV, so as to equal a desired voltage. By setting the detected CMV equal to Vcc/2, for example, the CMV feedback circuit may position the electrode potentials for maximum headroom. The CMV feedback circuit may be implemented in any known manner. In one embodiment, the CMV feedback circuit may include a voltage divider circuit coupled for detecting the CMV across the outer electrodes, and a comparator coupled for setting the detected CMV (vcm_in) equal to a desired voltage (vcm_set) and supplying a CMV control signal (vcm_control) to the bottom current source.

In the receive stage 330, amplifier 370 is coupled for receiving the modulated voltage waveform ($V_O$) from the load 310 and configured for producing an amplified voltage waveform ($V_O'$), which is supplied to filter 380. The modulated voltage waveform ($V_O$) may be a bio-impedance signal detected across the inner electrodes (EL2 and EL3), or a skin-electrode contact quality signal detected across the outer electrodes (EL1 and EL4), as described above.

According to one embodiment, amplifier 370 may be an instrumentation amplifier (IA) or a voltage gain amplifier (VGA) having a programmable gain (e.g., between about 0 dB to about 90 dB) and a programmable reference voltage (REF). According to one embodiment, filter 380 may be an anti-aliasing filter, which is configured to limit the bandwidth of the filtered waveform ($V_O''$) supplied to the ADC 390. In some embodiments, the gain of the instrumentation amplifier 370 may be set to bring the filtered waveform ($V_O''$) to full scale, so as to maximize the signal-to-noise ratio of the ADC.

Figure 4:
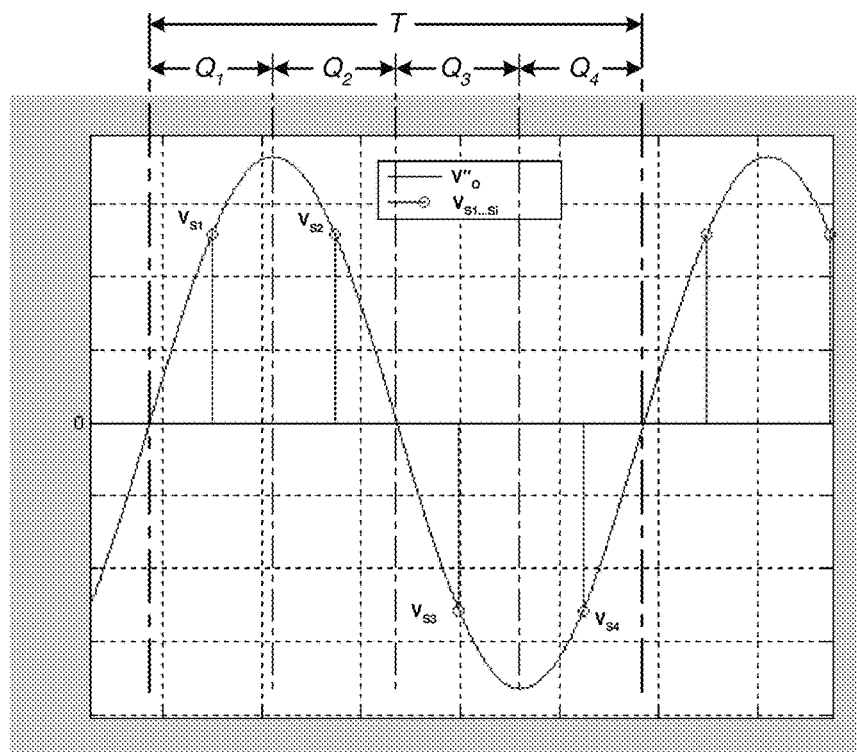
FIG. 4 is a graph illustrating one manner in which an analog-to-digital converter (ADC) may be used to generate four digital samples ($V_{S1}$, $V_{S2}$, $V_{S3}$, $V_{S4}$) from an output waveform ($V_0''$), such that one digital sample is generated within each ($Q_1$, $Q_2$, $Q_3$, $Q_4$) of the output waveform.

ADC 390 is coupled for receiving the filtered waveform ($V_O''$) output from filter 380 and is generally configured for producing a number of digital samples ($V_S$) therefrom. According to one embodiment, ADC 390 may be a $\Sigma\Delta$ ADC (or SD-ADC), which is specifically configured to generate four digital samples ($V_{S1}, V_{S2}, V_{S3}, V_{S4}$), each spaced 90° apart, for every period (T) of the filtered output waveform ($V_O''$), as described above. Stated another way, ADC 390 may be specifically configured to generate four digital samples ($V_{S1}, V_{S2}, V_{S3}, V_{S4}$) from the filtered output waveform ($V_O''$), so that one digital sample is generated within each quadrant ($Q_1, Q_2, Q_3, Q_4$) of the filtered output waveform ($V_O''$), as shown in FIG. 4 and described above.

Controller 340 is generally coupled and configured for controlling the operation of the transmit stage 320 and receive stage 330. On the transmit side, controller 340 is coupled for supplying a control signal (CTL) to waveform generator 350 for generating a sinusoidal varying injection current signal ($I_{IN}$) having a programmable input frequency ($F_{IN}$), amplitude (A) and phase. On the receive side, controller 340 is coupled for controlling the operation of ADC 390, such that the oversampling rate (OSR) and the decimation rate (DR) of the ADC is matched to a particular input frequency ($F_{IN}$) chosen for monitoring the bio-impedance signal. According to one embodiment, controller 340 may be a microcontroller unit (MCU) or other on-chip controller or processing device. Such a controller may include, or may have access to, a memory component comprising a table of stored values, which may be used to control or adjust the oversampling rate (OSR) and decimation rate (DR) of the ADC, according to the input frequency ($F_{IN}$) chosen for monitoring the bio-impedance signal. An example embodiment of such a table is illustrated in FIG. 5 and described above.

In some embodiments, the digital samples ($V_{S1}, V_{S2}, V_{S3}, V_{S4}$) generated by ADC 390 may be supplied directly to controller 340 for extracting magnitude and phase information from the filtered output waveform ($V_O''$) according to equations (3) and (4) above. In other embodiments, controller 340 may average the digital samples ($V_{S1}, V_{S2}, V_{S3}, V_{S4}$) generated by ADC 390 over a number (P) of periods prior to extracting magnitude and phase information according to equations (5) and (6) above. While not necessary for all input frequencies, averaging the digital samples over a number (P) of periods reduces the bandwidth of the ADC quantization noise by a factor of P, and thus, may be used to recover ADC resolution loss caused, for example, by reducing the OSR of the ADC to a lower ("valid") OSR at lower input frequencies. Alternatively, the digital samples may be averaged to reduce observation time and power consumption of the synchronous detection circuit.

Figure 7:
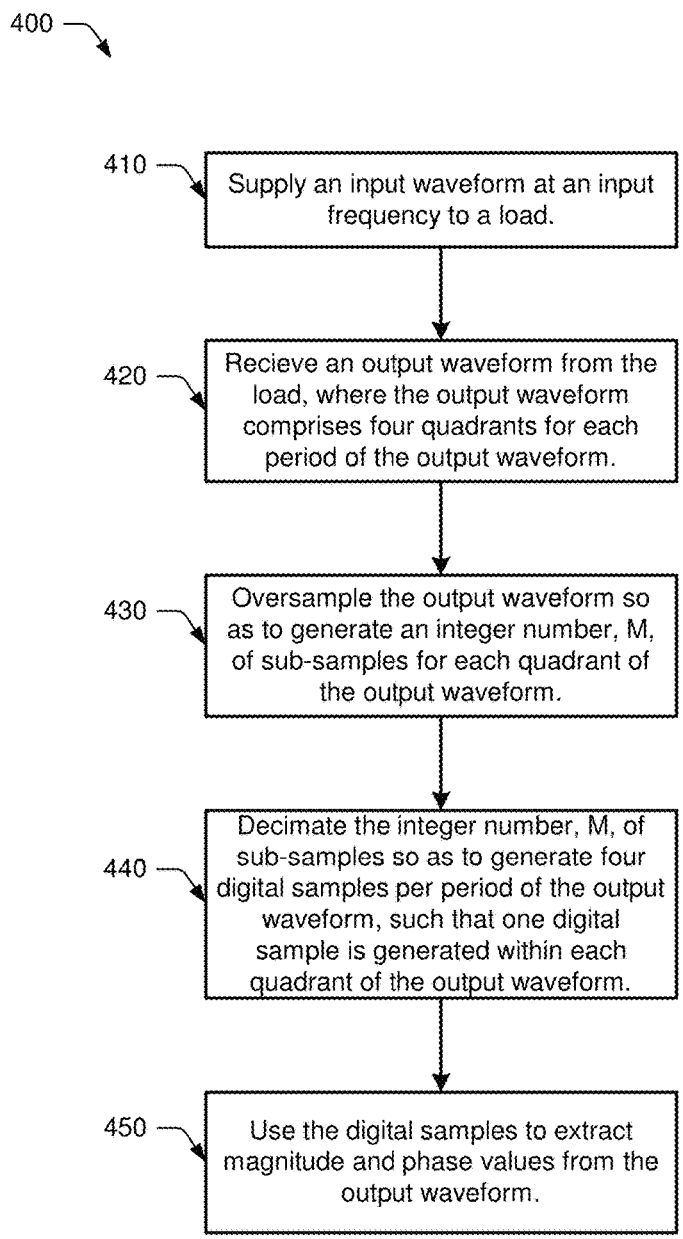
FIG. 7 is a flowchart diagram illustrating one embodiment of a method for extracting magnitude and phase from a waveform.

FIG. 7 is a flowchart diagram illustrating one embodiment of a method 400 for extracting magnitude and phase from a waveform. The method 400 described herein may be performed by embodiments of the synchronous detection circuit described herein, or an alternate yet functionally equivalent synchronous detection circuit. The disclosed method may be broadly used for extracting magnitude and phase information from substantially any amplitude and/or phase modulated waveform. According to one particular embodiment, the disclosed method may be used for determining the bio-impedance of a biological tissue by extracting magnitude and phase information from a bio-impedance voltage waveform.

In some embodiments, method 400 may begin by supplying an input waveform at an input frequency to a load (step 410) and receiving an output waveform from the load (step 420). When used for detecting bio-impedance, the input waveform may be an alternating current signal, which is supplied to a first pair of electrodes in contact with the biological tissue, and the output waveform may be a voltage waveform received from a second pair of electrodes in contact with the biological tissue. When used for detecting other types of signals, the input and output waveforms may comprise other types of waveforms. Regardless, the output waveform received in step 420 may include four quadrants for each period of the output waveform.

In some embodiments, the method 400 may include selecting the input frequency from a range of available input frequencies prior to the step of supplying the input waveform to the load. In one example, the range of available input frequencies may comprise about 1 kHz to about 100 kHz, as these input frequencies are commonly used for detecting bio-impedance. In some embodiments, the method 400 may be performed at a single input frequency, or may be performed repeatedly over a plurality of input frequencies. Although described herein as comprising a particular range of input frequencies, the input frequency of the input waveform is not strictly limited to only the disclosed frequencies. Alternative frequency ranges may be appropriate depending on the application or use of the synchronous detection circuit.

Subsequent to receiving the output waveform (in step 420), the method may include oversampling the output waveform so as to generate an integer number, M, of sub-samples for each quadrant of the output waveform (step 430), and decimating the integer number, M, of sub-samples, so as to generate four digital samples per period of the output waveform, such that one digital sample is generated within each quadrant (step 440). The steps of oversampling and decimating may generally be performed by an analog-to-digital converter (ADC), which in one embodiment, may be a ΣΔ-ADC. In step 450, the method may use the digital samples generated by the ADC in step 440 to extract magnitude and phase values from the output waveform.

In some embodiments, the method may use the four digital samples generated each period of the output waveform to calculate new magnitude and phase values every period of the output waveform in accordance with equations (3) and (4) above. In other embodiments, the method may average the four digital samples generated over a number, P, of periods of the output waveform, and may use the averaged digital samples to calculate new magnitude and phase values every P periods of the output waveform in accordance with equations (5) and (6) above.

In some embodiments, a clock signal having a fixed clock frequency may be supplied to the ADC for generating the integer number, M, of sub-samples in synchronization with the clock signal. In such embodiments, the integer number, M, may be proportional to the fixed clock frequency and inversely proportional to the input frequency of the input waveform. In some embodiments, the integer number, M, may be substantially equal to the fixed clock frequency divided by 4N times the input frequency, where N is an integer number greater than or equal to 1.

Prior to the steps of oversampling and decimating, some embodiments of the method may include setting an oversampling rate (OSR) of the ADC equal to a decimating rate (DR) of the ADC, so that the ADC generates the integer number, M, of sub-samples and the one digital sample for each quadrant of the voltage waveform. In general, the OSR and the DR of the ADC may be set equal to an integer multiple of the integer number, M.

As noted above, the input frequency of the input waveform may be programmable in some embodiments, and may be selected from a range of input frequencies (e.g., about 1 kHz to about 100 kHz). In such embodiments, the integer multiple may change with changes in input frequency. For example, the OSR and the DR of the ADC may be set equal to N times M for a first subset of input frequencies (e.g., frequencies of 20 kHz and above) within the range of input frequencies, where N is an integer number greater than or equal to 1. On the other hand, the OSR of the ADC may be set equal to N times M divided by X, where X is an integer number greater than or equal to 2, for a second subset of input frequencies (e.g., frequencies below 20 kHz) within the range of input frequencies. The DR of the ADC may remain equal to N times M for the second subset of input frequencies. Setting the OSR and DR of the ADC in such a manner may enable the ADC to output continuous time averaged samples, of 1 or more digital samples per quadrant, without artifacts and without exceeding the limitations of the ADC.

It will be appreciated to those skilled in the art that this disclosure is believed to provide an improved synchronous detection circuits and methods for extracting magnitude and phase information from a waveform. In some embodiments, the synchronous detection circuits and methods described herein may be used for detecting and monitoring of bio-impedance signals, and may be incorporated within a biometric monitoring device. However, the synchronous detection circuits and methods described herein are not strictly limited to such, and may be used for detecting/monitoring other types of modulated signals.

As noted above, the synchronous detection circuits and methods disclosed herein provide many advantages over conventional synchronous detection circuits and methods, such as high efficiency, low power and low cost, while providing high accuracy and measurement reliability for an almost infinite range of programmable excitation/carrier frequencies. Other advantages/distinctions will be apparent to the skilled artisan upon reading this disclosure.

Further modifications and alternative embodiments of various aspects of the disclosure will also be apparent to those skilled in the art in view of this description. It is to be understood that the various embodiments of synchronous detection circuits, methods and biometric monitoring devices comprising such circuits and methods are to be taken as the presently preferred embodiments. Elements and materials may be substituted for those illustrated and described herein, parts and processes may be reversed, and certain features of the synchronous detection circuits described herein may be utilized independently, all as would be apparent to one skilled in the art after having the benefit of this disclosure. It is intended, therefore, that the following claims be interpreted to embrace all such modifications and changes and, accordingly, the specification and drawings are to be regarded in an illustrative rather than a restrictive sense.

What is claimed is:

1. A synchronous detection circuit configured to determine a bio-impedance of a biological tissue, the synchronous detection circuit comprising:
   a driver circuit configured to be coupled to the biological tissue, the driver circuit supplying an alternating current signal at an input frequency to a first pair of electrodes in contact with the biological tissue;
   an analog-to-digital converter (ADC) configured to be coupled to the biological tissue, the ADC receiving a voltage waveform from a second pair of electrodes in contact with the biological tissue, wherein each period of the voltage waveform comprises four quadrants, and wherein the ADC is configured for generating four digital samples per period of the voltage waveform, such that one digital sample is generated within each of the four quadrants; and
   a controller coupled to the ADC, the controller configured for:
      setting an oversampling rate (OSR) of the ADC, so that the ADC generates an integer number, M, of sub-samples during each quadrant of the voltage waveform, wherein the integer number, M, of sub-samples is inversely proportional to the input frequency of the alternating current signal; and
      determining the bio-impedance of the biological tissue by using the digital samples generated by the ADC to determine a magnitude and a phase of the voltage waveform.

2. The synchronous detection circuit as recited in claim 1, wherein the controller is configured for using the four digital samples generated per period of the voltage waveform to calculate new magnitude and phase values every period of the voltage waveform.

3. The synchronous detection circuit as recited in claim 1, wherein the controller is configured for:

averaging the four digital samples generated over a number, P, of periods of the voltage waveform; and using the averaged digital samples to calculate new magnitude and phase values every P periods of the voltage waveform.

4. The synchronous detection circuit as recited in claim 1, wherein the controller is further configured for setting a decimating rate (DR) of the ADC equal to the oversampling rate (OSR) of the ADC, so that the ADC generates one digital sample for every M number of sub-samples.

5. The synchronous detection circuit as recited in claim 4, wherein the ADC is configured for generating the digital samples and the sub-samples in synchronization with a clock signal having a fixed clock frequency, and wherein the integer number, M, of sub-samples is proportional to the fixed clock frequency and inversely proportional to the input frequency of the alternating current signal.

6. The synchronous detection circuit as recited in claim 5, wherein the integer number, M, of sub-samples is substantially equal to the fixed clock frequency divided by 4N times the input frequency, where N is an integer number greater than or equal to 1.

7. The synchronous detection circuit as recited in claim 4, wherein the controller is configured for setting the OSR and the DR of the ADC equal to an integer multiple of the integer number, M, wherein the input frequency of the alternating current signal is programmable and selected by the controller from a range of input frequencies, and wherein the integer multiple changes with changes in input frequency.

8. The synchronous detection circuit as recited in claim 7, wherein the controller is configured for setting the OSR and the DR of the ADC equal to N times M for input frequencies of 20 kHz and above, where N is an integer number greater than or equal to 1.

9. The synchronous detection circuit as recited in claim 7, wherein the controller is configured for setting the OSR of the ADC equal to N times M divided by X for input frequencies below 20 kHz, where X is an integer number greater than or equal to 2.

10. The synchronous detection circuit as recited in claim 7, further comprising a memory component configured for storing a table of values comprising predetermined values of M, N and OSR for each input frequency within the range of input frequencies, and wherein the controller is configured for using the table of values to set the OSR and the DR of the ADC.

11. The synchronous detection circuit as recited in claim 1, further comprising a waveform generator coupled to the driver circuit, the waveform generator configured for generating a sinusoidal waveform at a programmable input frequency and phase, and coupled to the driver circuit for supplying the sinusoidal waveform to the driver circuit for generating the alternating current signal.

12. The synchronous detection circuit as recited in claim 11, wherein the waveform generator is further coupled for supplying a digital signal to the driver circuit for controlling an amplitude of the alternating current signal.

13. The synchronous detection circuit as recited in claim 12, wherein the driver circuit comprises a current-controlled, digital-to-analog converter (I-DAC) having a number of programmable current amplitudes selectable by the digital signal.

14. The synchronous detection circuit as recited in claim 1, further comprising a common mode voltage (CMV) feedback circuit coupled for sensing a CMV between the first pair of electrodes, and further coupled to the driver circuit for setting the CMV equal to a desired voltage.

15. A method for determining a bio-impedance of a biological tissue, the method comprising:
    supplying an alternating current signal at an input frequency to a first pair of electrodes in contact with the biological tissue;
    receiving a voltage waveform from a second pair of electrodes in contact with the biological tissue, wherein the voltage waveform comprises four quadrants for each period of the voltage waveform;
    oversampling the voltage waveform so as to generate an integer number, M, of sub-samples for each quadrant of the voltage waveform, wherein the integer number, M, is inversely proportional to the input frequency of the alternating current signal;
    decimating the integer number, M, of sub-samples so as to generate four digital samples per period of the voltage waveform, such that one digital sample is generated within each quadrant; and
    using the digital samples to extract magnitude and phase values from the voltage waveform to determine the bio-impedance of the biological tissue.

16. The method as recited in claim 15, wherein prior to the step of supplying an alternating current signal, the method further comprises selecting the input frequency from a range of available input frequencies comprising about 1 kHz to about 100 kHz.

17. The method as recited in claim 16, wherein prior to the steps of oversampling and decimating, the method further comprises setting an oversampling rate (OSR) of an analog-to-digital converter (ADC) equal to a decimating rate (DR) of the ADC, so that the ADC generates the integer number, M, of sub-samples and the one digital sample for each quadrant of the voltage waveform.

18. The method as recited in claim 17, wherein the step of the setting the OSR and the DR of the ADC comprises setting the OSR and the DR equal to an integer multiple of the integer number, M, and wherein the integer multiple depends on the input frequency selected from the range of available input frequencies.

19. The method as recited in claim 17, wherein the step of the setting the OSR and the DR of the ADC comprises setting the OSR and the DR equal to N times M for input frequencies of 20 kHz and above, where N is an integer number greater than or equal to 1.

20. The method as recited in claim 17, wherein the step of the setting the OSR and the DR of the ADC comprises setting the OSR equal to N times M divided by X, where X is an integer number greater than or equal to 2, and setting the DR equal to N times M, for input frequencies below 20 kHz.

21. The method as recited in claim 15, wherein the step of using the digital samples comprises using the four digital samples generated per period of the voltage waveform to calculate new magnitude and phase values every period of the voltage waveform.

22. The method as recited in claim 15, wherein the step of using the digital samples comprises:
    averaging the four digital samples generated over a number, P, of periods of the voltage waveform; and
    using the averaged digital samples to calculate new magnitude and phase values every P periods of the voltage waveform.

* * * * *